United States Patent
Zhao (10) Patent No.: US 10,179,006 B2
(45) Date of Patent: Jan. 15, 2019

(54) DISPOSABLE CIRCUMCISION ANASTOMAT

(71) Applicant: Yongjiu Zhao, Zhejiang (CN)

(72) Inventor: Yongjiu Zhao, Zhejiang (CN)

(*) Notice: Subject to any disclaimer, the term of this patent is extended or adjusted under 35 U.S.C. 154(b) by 187 days.

(21) Appl. No.: 15/115,683

(22) PCT Filed: Jun. 14, 2015

(86) PCT No.: PCT/CN2015/078913
§ 371 (c)(1),
(2) Date: Jul. 31, 2016

(87) PCT Pub. No.: WO2016/090845
PCT Pub. Date: Jun. 16, 2012

(65) Prior Publication Data
US 2017/0020547 A1 Jan. 26, 2017

(30) Foreign Application Priority Data
Dec. 12, 2014 (CN) .......................... 2014 1 0760090

(51) Int. Cl.
*A61B 17/326* (2006.01)

(52) U.S. Cl.
CPC .................. *A61B 17/326* (2013.01)

(58) Field of Classification Search
CPC ....... A61B 17/326; B32B 21/04; B32B 21/06; B32B 21/14; B32B 21/145
See application file for complete search history.

(56) References Cited

U.S. PATENT DOCUMENTS

2012/0277759 A1* 11/2012 Shang ................ A61B 17/326
606/118

FOREIGN PATENT DOCUMENTS

| CN | 1463677 A | 12/2003 | |
|---|---|---|---|
| CN | 101066223 A | 11/2007 | |
| CN | 201861722 | 6/2011 | |
| CN | 102370511 | 3/2012 | |
| CN | 102451031 | 5/2012 | |
| CN | 202604965 | 12/2012 | |
| CN | 201210497584.9 | 3/2013 | |
| CN | 102370511 B | 7/2013 | |
| CN | 104490455 | 4/2015 | |
| CN | 204351900 | 5/2015 | |
| WO | WO 2013/173804 | * 11/2013 | ........... A61B 17/326 |

* cited by examiner

*Primary Examiner* — Thomas McEvoy (57) ABSTRACT

A disposable circumcision anastomat includes: an inner ring (2) and an outer ring (1) corresponding to the inner ring (2); wherein the outer ring (1) includes arc sidewalls, and the arc sidewalls are connected to arc blades (7); a loop blade faces inwards; convex structures (8) are repeatedly arranged at internal portion of the outer ring (1) for fixing, and the arc blades (7) form containing spaces (6) with the convex structures (8). With the disposable circumcision anastomat for removing redundant prepuce or phimosis, incision is neat, postoperative bleeding hardly happens, operation is easy, operation time is short, healing is fast, side effects is slight, patients suffer less, and postoperative recovery is fast.

12 Claims, 8 Drawing Sheets

DISPOSABLE CIRCUMCISION ANASTOMAT

CROSS REFERENCE OF RELATED APPLICATION

This is a U.S. National Stage under 35 U.S.C. 371 of the International Application PCT/CN2015/078913, filed Mar. 14, 2015, which claims priority under 35 U.S.C. 119(a-d) to CN 201410760090.4, filed Dec. 12, 2014.

BACKGROUND OF THE PRESENT INVENTION

Field of Invention

The present invention relates to a field of medical devices, and more particularly to a circumcision device with neat incision, hardly postoperative bleeding, easy operation, short operation time, and fast healing.

Description of Related Arts

Redundant prepuce or phimosis is a common disease of urology, which is likely to cause urinary tract infections, prostatitis and other diseases, and is a way to spread venereal diseases. Therefore, removal of the redundant prepuce or phimosis is one of the methods to prevent such diseases. Conventionally, the redundant prepuce or phimosis is surgically resected. Chinese patent CN101066223A discloses a circumcision aid and a surgical method therefore, wherein the method comprises preoperative preparation, local anesthesia, placing the circumcision aid, fixing the circumcision aid, cutting protruding prepuce, suturing, hemostatic dressing, stitching and other steps. Disadvantages thereof are: no neat incision, easily postoperative bleeding, and complex operation. Then there was a surgical instrument for prepuce natural shedding due to avascular necrosis, as disclosed in Chinese patent CN1463677A, wherein a disclosed bicyclic circumcision device comprises an outer ring, an inner ring and a nesting device. The device has a variety of sizes. During operation, the excess part of the prepuce is placed between the inner and outer rings, in such a manner that a far side of the prepuce suffers from avascular necrosis, while a close side of the prepuce gradually heals between inner and outer plates. 8-12 days after surgery, the far side of the prepuce falls off with the inner and outer rings, so as to achieve prepuce circumcision. Disadvantages thereof are: prepuce edema is easy to happen, patient pain is obvious, necrotic tissue falls off slowly, wound heals slowly, and postoperative care is difficult.

Referring to Chinese patent CN102370511B, inventors thereof had conducted related improvements, wherein: a disposable circumcision anastomat comprises an inner ring and a corresponding outer ring. The outer ring has a sidewall connecting to a blade and has a receiving portion for receiving a gasket. The receiving portion comprises a plurality of engagement strips inwardly extending from the sidewall, and widths of the engagement strip are smaller than a width of the blade. The engagement strips form a receiving space with the adjacent blade. However, a structure of the engagement strips is not specifically designed for fitting a glans structure. The glans is not a smooth plane, so engaging with a flat square engagement strip will cause integrated engagement to engaged organization and airtight, in such a manner that blood cannot flow through the integrated engagement portion. Meanwhile, non-engagement portion has a large overall gap, and the anastomat is not thoroughly and tightly engaged with the prepuce tissue, leading to easy falling off. For some occasions, if an engagement strip width is limited to be less than the width of the blade, engagement results may also worse than ideal ones. With the device of the above invention, patients are easy to suffer from prepuce edema and prepuce splitting. Postoperative pain is significant, necrotic tissue falls off slowly, and wound heals slowly. In some severe cases, the patients need a secondary surgery with a traditional method to heal. Thus, products according to the above invention have not been sufficiently applied in clinical practice.

Chinese patent application CN201210497584.9 adopts a novel cartridge structure for containing staple with a wider cross-section. The staple is U-shaped with nails at both ends. An enlarged nail bridge is connected between ends of the nails for a circumcision device. The staple of the circumcision device pierces through target tissues with an external force, and forms a chamfer with a chamfer metal ring, so as to suture. Due to a large area of the nail bridge of each staple, when being pushed forwards for forming the chamfer, the staple bears an even force with a stable direction and accuracy positioning. Furthermore, tissue-wrapping is avoided, which is conducive to postoperative falling off. Although products of the above invention have many advantages and have been widely used, the following conditions may happen in clinical application: 1) during operation, the staple may fall off and tissues may bleed, which requires stitching; 2) after operation, the staple may be not fixed strong enough and the tissues may bleed due to slippage, causing hematoma and prepuce splitting, which requires a secondary surgery; 3) after operation, the staple falls off slowly, which lowers living quality of patient.

There are a lot of inventions related to medical devices which lack consideration about clinical experience and patient care, so in clinical use, the surgical procedure clinician and patient can still find the flaws, and even feel discomfort or pain. Therefore, it is a serious problem to design a circumcision device with neat incision, hardly postoperative bleeding, easy operation, short operation time, fast healing, and less pain.

SUMMARY OF THE PRESENT INVENTION

An object of the present invention is to overcome disadvantages of conventional circumcision surgeries such as no neat incision, easily postoperative bleeding, complex operation, and long operation time; and provide a disposable circumcision anastomat with neat incision, hardly postoperative bleeding, easy operation, short operation time, and fast healing.

Accordingly, in order to accomplish the above object, the present invention provides a disposable circumcision anastomat, comprising: an inner ring and an outer ring corresponding to the inner ring; wherein the outer ring has an outer ring opening; a corresponding closure structure is provided at the outer ring opening, which overlaps for forming a smooth closure; wherein the outer ring comprises a plurality of arc structures hinged to each other; the arc structures comprises arc sidewalls, and the arc sidewalls are connected to arc blades; a loop blade is formed by a plurality of the arc blades with cutting edges facing inwards; convex structures, which extend towards a loop center, are repeatedly arranged on the arc sidewalls, and a width of each of the convex structures is no wider than a width of any of the arc blades; the arc blades form containing spaces with the convex structures.

The present invention also provides a disposable circumcision anastomat, comprising: an inner ring, an outer ring corresponding to the inner ring, and an elastic gasket between the inner ring and the outer ring; wherein the outer ring has an outer ring opening; a corresponding closure structure is provided at the outer ring opening, which overlaps for forming a smooth closure; wherein the outer ring comprises a plurality of arc structures hinged to each other; the arc structures comprises arc sidewalls, and the arc sidewalls are connected to arc blades; a loop blade is formed by a plurality of the arc blades with cutting edges facing inwards; convex structures, which extend towards a loop center, are repeatedly arranged on the arc sidewalls; a width of each of the convex structures is no wider than a combination of a width of any of the arc blades and a thickness of the elastic gasket, and is no narrower than a difference of the width of any of the arc blades and the thickness of the elastic gasket; the arc blades form containing spaces with the convex structures.

Preferably, the arc blades form smooth arc containing spaces with the convex structures.

Preferably, the convex structures on the arc blades are jagged, triangular, spike or conical.

Preferably, the convex structures on the arc blades are repeatedly arranged with an interval of 1.0-10.0 mm.

Preferably, parallel distances between the arc blades and the convex structures are 1.5-6.0 mm.

Preferably, both upper edges and lower edges of external sidewalls of the inner ring have loop convexes and intermittent convexes.

Preferably, the outer ring is formed by two arc structures hinged to each other, wherein the arc structures are first arc structures; first ends of the first arc structures have arc transition structures, and second ends of the first arc structures have the corresponding closure structure.

Preferably, the outer ring is formed by no less than three arc structures hinged to each other, wherein the arc structures comprises a second arc structure and two first arc structures; first ends of the first arc structures have arc transition structures, and second ends of the first arc structures have the corresponding closure structure; both a first end and a second end of the second arc structure have the arc transition structures, wherein the arc transition structures at the first end of the second arc structure are placed at top faces of the arc blades, and the arc transition structures at the second end of the second arc structure are placed at lower faces of the arc blades.

Preferably, the disposable circumcision anastomat further comprises a fixing fiber, wherein the outer ring has at least two through-holes, and the through-holes are placed between the arc blades and the convex structures; the fixing fiber passes through one of the through-holes and bypasses the inner ring, then passes through the other of the through-holes.

Beneficial effects of the present invention are as follows. The arc blades are used for forming the loop blade, wherein the arc blades have effects such as cutting, fitting, and preventing bacterial infection. The convex structures are repeatedly arranged at internal portions of the inner ring, which extend towards the loop center from the sidewalls, which are parallel to a loop blade direction, of internal faces of the outer ring. Such convex structures have been continuously improved based on a large number of simulation experiments and clinical trials, wherein a design thereof fully fits a prepuce structure, for sufficient engagement. Furthermore, tight and accurate point-face fixing is achieved by convex points of a plurality of repeatedly arranged convex structures, so as to ensure smooth blood flow of tissues between the convex points for preventing tissue necrosis. The repeatedly arranged convex structures enable tight fixing and sufficient jointing between inner and outer prepuce plates, and avoid falling off and bleeding. The width of each of the convex structures is no wider than the width of any of the arc blades (when using the elastic gasket, the width of each of the convex structures is no wider than the combination of the width of any of the arc blades and the thickness of the elastic gasket, and is no narrower than the difference of the width of any of the arc blades and the thickness of the elastic gasket), which provides a sufficient blade engagement during cutting.

By using the disposable circumcision anastomat and corresponding equipments thereof for prepuce circumcision, incision is neat, postoperative bleeding hardly happens, operation is easy, and operation time is short. After removing the circumcision device, a prepuce surgery section is difficult to bleed, wound is smooth, and physical as well as mental health of the patient receives good care.

Conventional surgeries adopt suturing, leading to a long surgery time, no neat wound, and easy prepuce crack as well as bleeding. In addition, conventional anastomat products use traditional Chinese medical philosophy, which means the wound heals after tissue necrosis and slow falling off. The patient needs a long time to heal, which lowers living quality. The present invention cuts the prepuce and fits the wound with the disposable circumcision anastomat, in such a manner that fresh wounds closely connected and healing is fast.

These and other features the present invention will become apparent from the following detailed description and the accompanying drawings.

ELEMENT REFERENCE

1—outer ring, 2—inner ring, 3—first arc structure, 4—corresponding closure structure, 5—second arc structure, 6—containing space, 7—arc blade, 8—convex structure, 9—loop convex, 10—intermittent convex, 11—through-hole, 12—arc transition structure.

DETAILED DESCRIPTION OF THE PREFERRED EMBODIMENT

Figure 1:
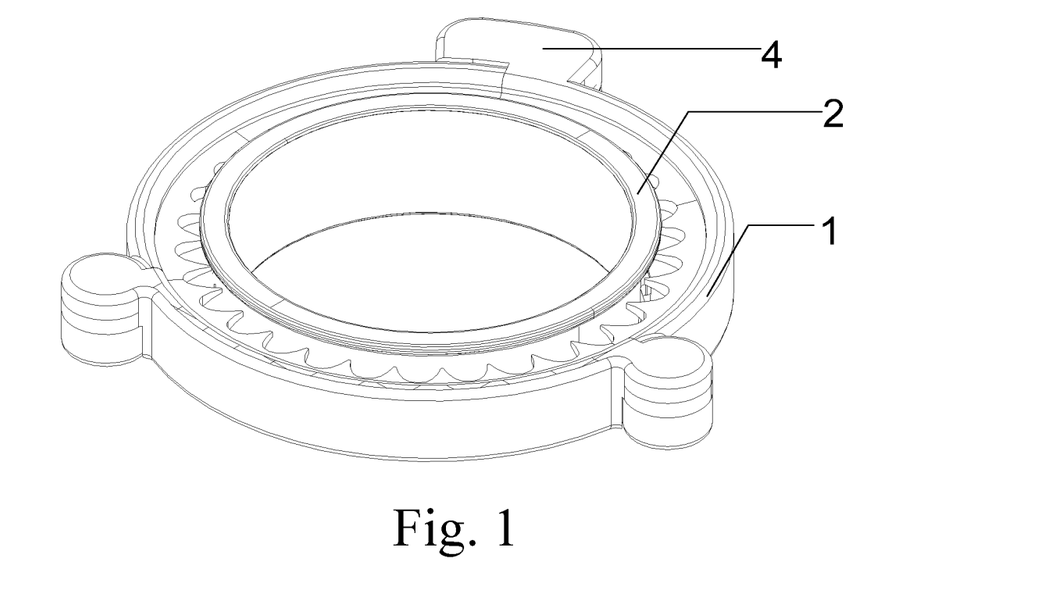
FIG. 1 is a perspective view of a disposable circumcision anastomat according to the present invention.
Figure 2:
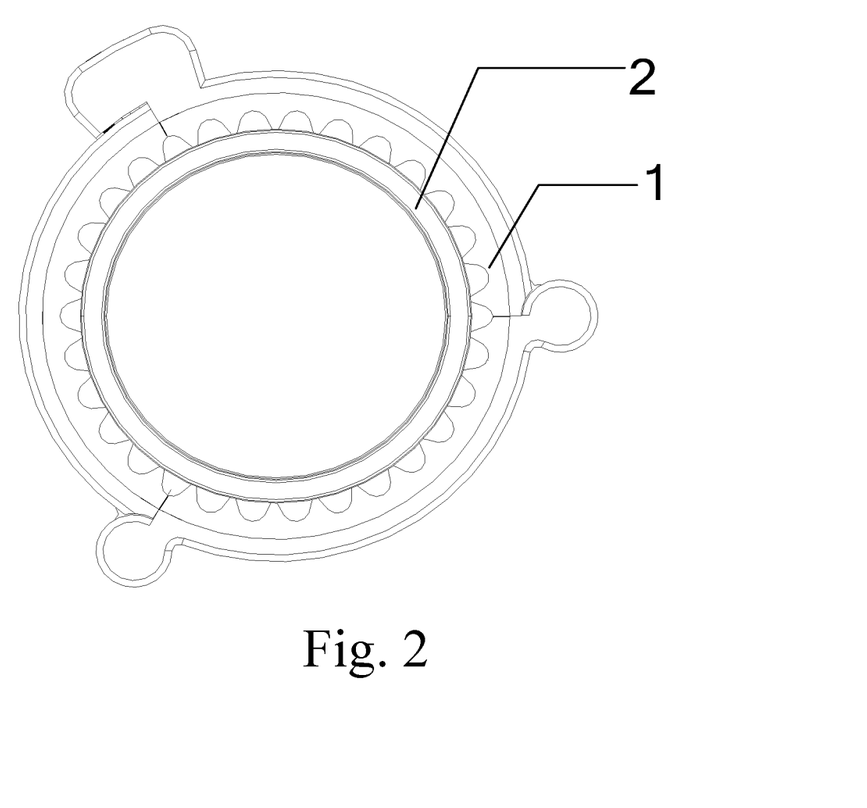
FIG. 2 is a top view of the disposable circumcision anastomat according to the present invention.
Figure 3:
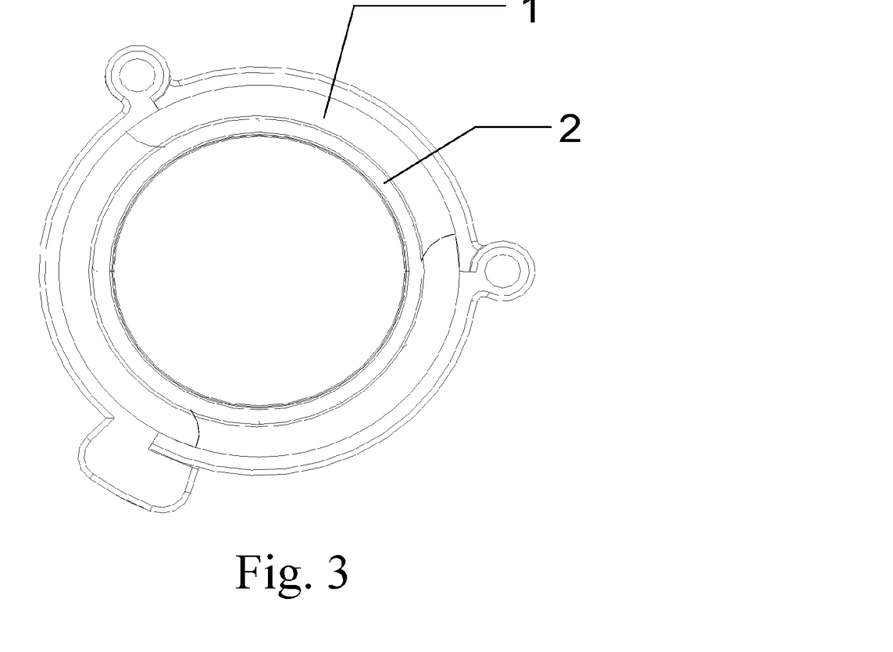
FIG. 3 is a bottom view of the disposable circumcision anastomat according to the present invention.

Referring to FIGS. 1-3 of the drawings, a disposable circumcision anastomat is illustrated, comprising: an inner ring 2 and an outer ring 1 corresponding to the inner ring 2; wherein a corresponding closure structure 4 is provided at an outer ring opening, which overlaps for forming a smooth closure. The disposable circumcision anastomat may further comprise an elastic gasket between the inner ring 2 and the outer ring 1.

Figure 5:
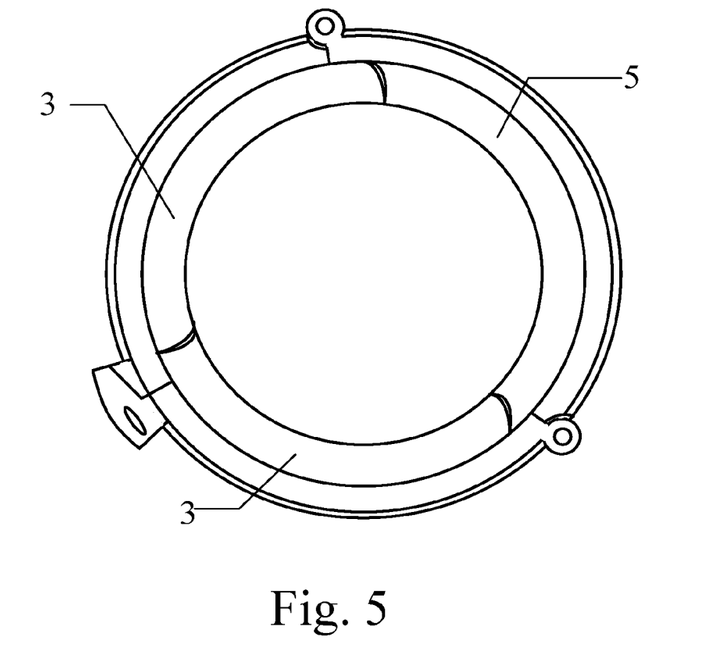
FIG. 5 is a bottom view of the outer ring.

Referring to FIG. 5, the outer ring 1 is formed by three arc structures hinged to each other (comprising two first arc structures 3 and a second arc structure 5). Besides, the outer ring 1 may be formed by two first arc structures 3, two first arc structures 3 and two second arc structures 5, or two first arc structures 3 and more second arc structures 5.

Figure 6:
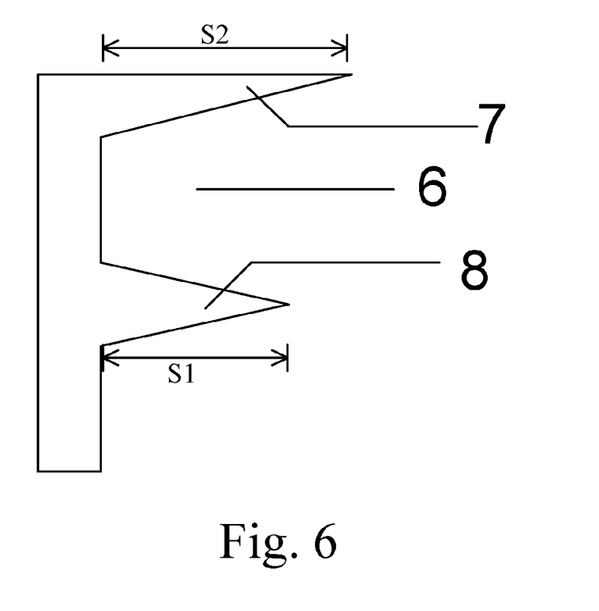
FIG. 6 is a longitudinal sectional view of the outer ring, wherein S1 illustrates a width of a convex structure and S2 illustrates a width of an arc blade.
Figure 7:
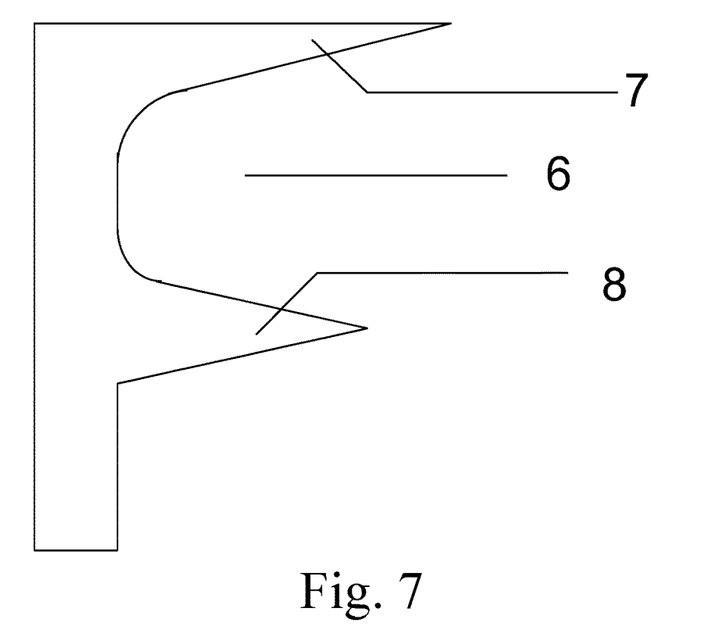
FIG. 7 is a longitudinal sectional view of the outer ring, wherein a containing space has an arc structure.

Referring to FIG. 6, the arc structures comprises arc sidewalls, and the arc sidewalls are connected to arc blades 7; a loop blade is formed by a plurality of the arc blades 7 with cutting edges facing inwards (as shown in FIG. 5); convex structures 8 are arranged on the arc sidewalls.

Figure 14:
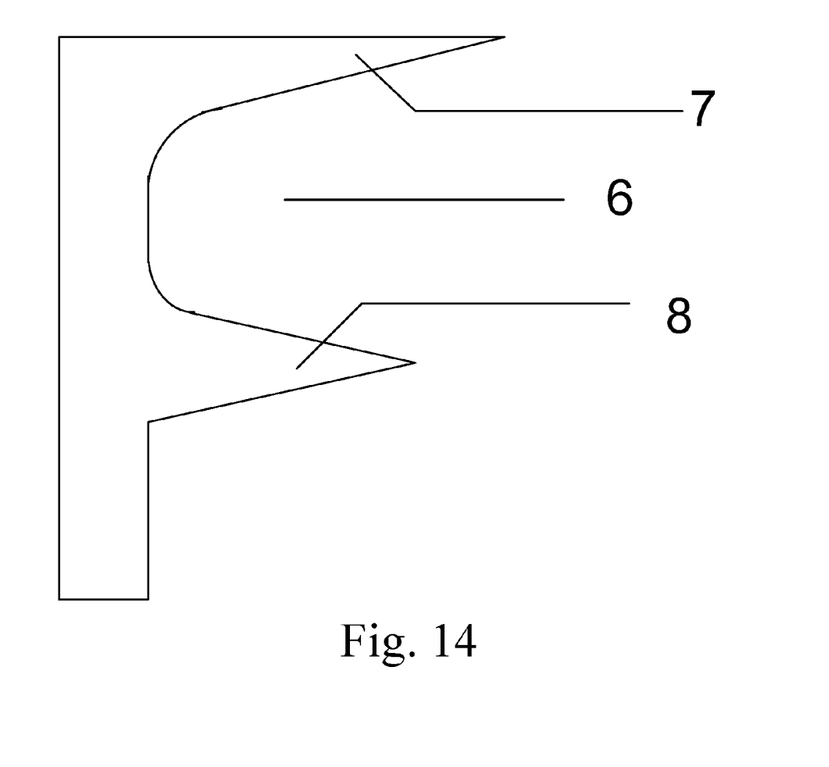
FIG. 14 is a longitudinal sectional view of the outer ring, wherein widths of the convex structure and the arc blade are identical (S1=S2).
Figure 15:
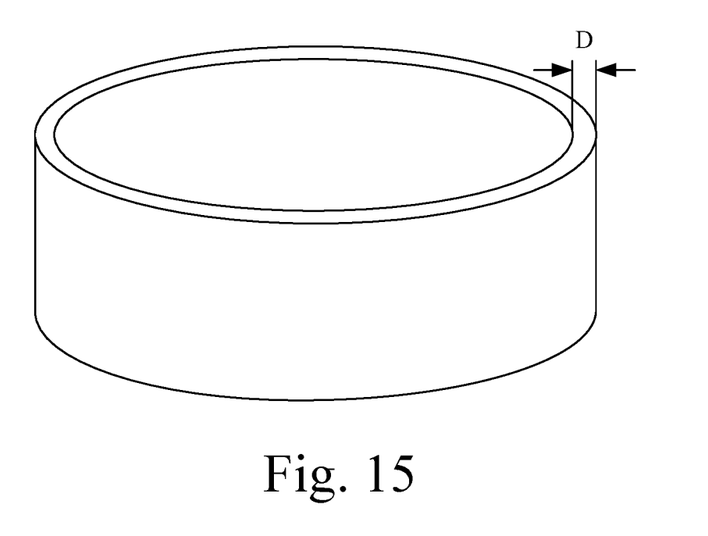
FIG. 15 is a sketch view of an elastic gasket, wherein D illustrates a width of the elastic gasket.

When the elastic gasket is not used by the disposable circumcision anastomat, a width S1 of each of the convex structures 8 is no wider than a width S2 of any of the arc blades 7, because if not, no sufficient cutting engagement can be provided. According to clinical researches, in practice of cutting prepuce tissues, when the width of the convex structures 8 equals to the width the arc blades 7, sufficient cutting engagement is also provided (as shown in FIG. 14).

When the elastic gasket is used by the disposable circumcision anastomat, a width of each of the convex structures 8 is no wider than a combination of a width of any of the arc blades 7 and a thickness of the elastic gasket, and is no narrower than a difference of the width of any of the arc blades 7 and the thickness of the elastic gasket. That is to say, S2−D≤S1≤S2+D. If S1<S2−D, when the arc blades 7 contact with the elastic gasket after cutting the prepuce, the convex structures 8 are still not able to touch the elastic gasket, resulting in no effect. If S1>S2+D, when the convex structures 8 presses into the elastic gasket and presses against the inner ring 2, the arc blades 7 are still not able to closely contact with the elastic gasket and the prepuce tissues, which means no sufficient cutting engagement.

Figure 4:
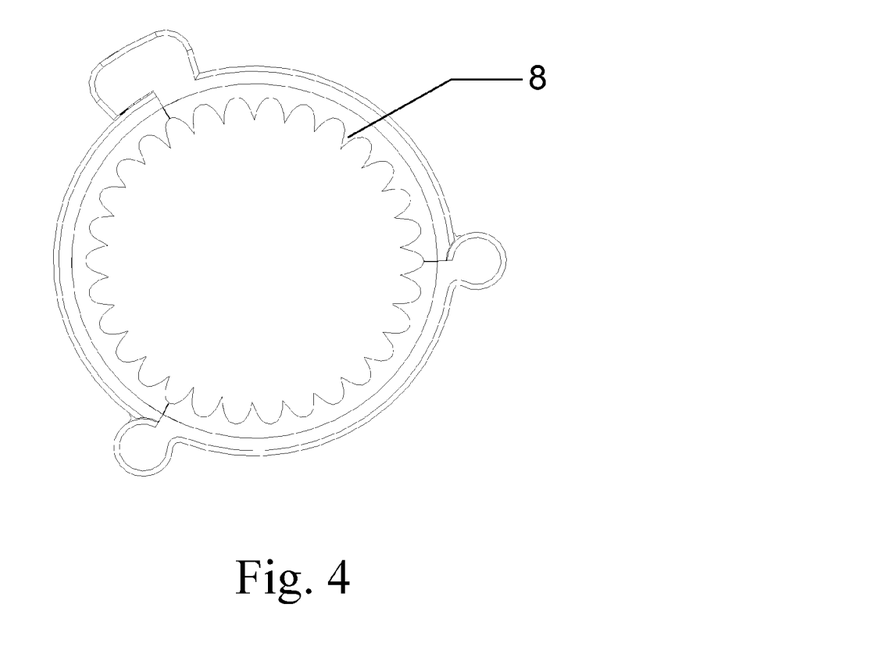
FIG. 4 is a top view of an outer ring.

Referring to FIG. 4, the convex structures 8 are repeatedly arranged on the arc sidewalls and extend towards a loop center.

When removing redundant prepuce or phimosis with the disposable circumcision anastomat, the inner ring 2 (if there is the elastic gasket, then the elastic gasket is sleeved outside the inner ring 2) is placed between a prepuce inner plate and a glans and adjusted. The outer ring 1 is placed at a position corresponding to the inner ring 2 and outer than a prepuce outer plate. The prepuce is adjusted to a proper position before tightening the corresponding closure structure 4. The redundant prepuce is cut with a blade along the loop blade. With the disposable circumcision anastomat for removing redundant prepuce or phimosis, incision is neat, postoperative bleeding hardly happens, operation is easy, and operation time is short. After removing the circumcision device, a prepuce surgery section is difficult to bleed, wound is smooth, and physical as well as mental health of the patient receives good care.

The convex structures 8 on the arc blades 7 are jagged, triangular, spike or conical. On one hand, the convex structures 8 provide a sufficient fixing effect, so as to enable tight fixing and sufficient jointing between the inner and outer prepuce plates, and avoid sliding or even falling off and bleeding. On the other hand, intervals between the convex structures 8 enable smooth blood flow when fixing tissues, avoiding tissue necrosis.

The convex structures 8 on the arc blades 7 are repeatedly arranged with an interval of 1.0-10.0 mm, so as to ensure sufficient fixing, for avoiding avascular necrosis at a far side of the fixed tissue or hidden dangers such as prepuce cracking and bleeding due to unstable fixing and easy falling off, thus providing a relative aesthetic surgical result.

The arc blades 7 have effects such as cutting, fitting, and preventing bacterial infection. During operation, the convex structures 8 fix the tissues, and the arc blades 7 cooperate with the inner ring 2 and the outer elastic gasket for cutting the prepuce tissues. Meanwhile, cutting wounds of the inner and outer prepuce plates are neatly engaged for achieving engagement. After cutting, the arc blades 7 and the external sidewalls of the inner ring 2 form a relatively sealed face (when using the elastic gasket, the arc blades 7 may form the relatively sealed face with the elastic gasket and the external sidewalls of the inner ring 2), wherein the relatively sealed face provides better protection to the cutting wounds of the prepuce, and prevents bacterial infection.

Referring to FIG. 6, the convex structures 8 may be placed at any position on the arc sidewalls, and there are certain intervals between the arc blades 7 and the convex structures 8, so as to form containing spaces 6 therebetween. If the containing spaces 6 formed by the arc blades 7 and the convex structures 8 are smooth arc as shown in FIG. 8, then smooth transition is provided to the inner and outer prepuce plates, which promotes wound healing and further improves the aesthetic surgical result.

Parallel distances between the arc blades 7 and the convex structures 8 may be 1.5-6.0 mm, in such a manner that tissue binding is extremely tight, no falling off happens, and postoperative prepuce length is proper. Fixed prepuce tissue falling off, bleeding or improper postoperative prepuce length is avoided as much as possible, so as to achieve a desired outcome.

Figure 8:
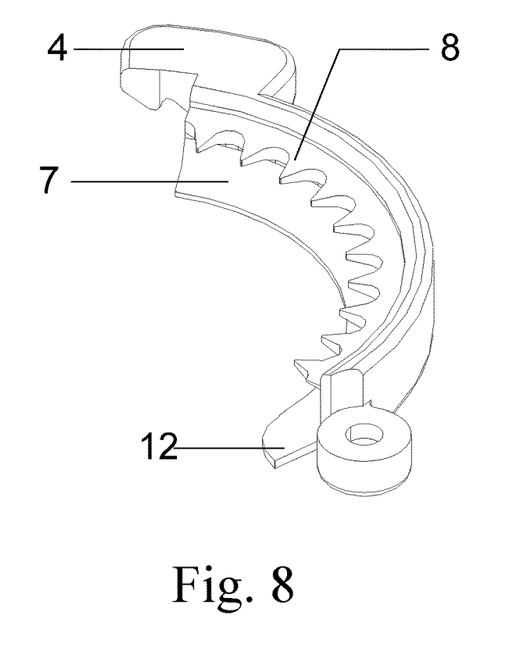
FIG. 8 is a sketch view of a first arc structure.
Figure 9:
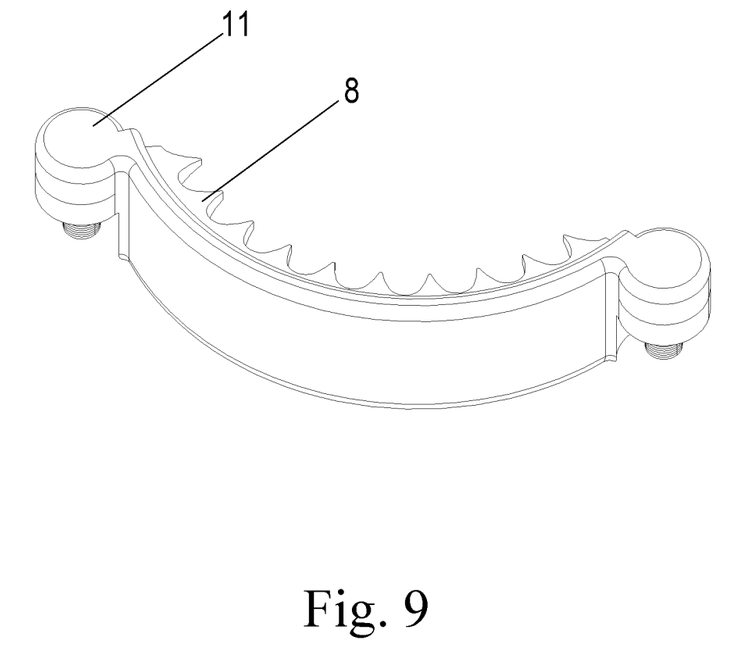
FIG. 9 is a sketch view of a second arc structure.
Figure 10:
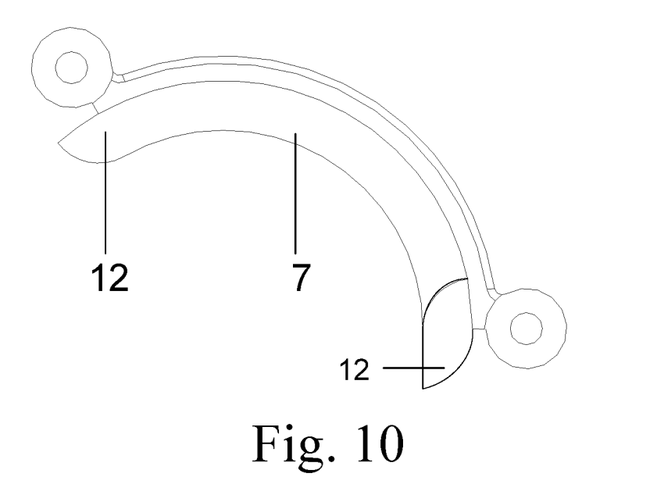
FIG. 10 is a top view of the second arc structure.

Referring to FIG. 8, first ends of the first arc structures 3 have arc transition structures 12, and second ends of the first arc structures 3 have the corresponding closure structure 4. Referring to FIGS. 9 and 10, both a first end and a second end of the second arc structure 5 have the arc transition structures 12, wherein the arc transition structures 12 at the first end of the second arc structure 5 are placed at top faces of the arc blades 7, and the arc transition structures 12 at the second end of the second arc structure 5 are placed at lower faces of the arc blades 7. The arc transition structures 12 enable smooth closure of edges of the arc blades 7, so as to prevent the prepuce tissues from being clutched in a joint portion of the loop blade.

Figure 11:
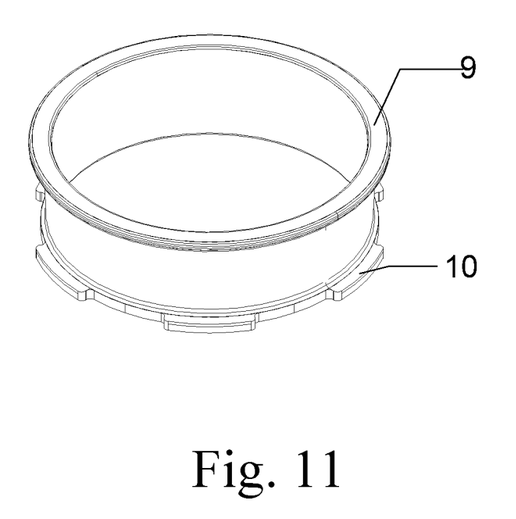
FIG. 11 is a sketch view of an inner ring, wherein upper edges of external sidewalls of the inner ring have loop convexes, and lower edges of the external sidewalls of the inner ring have intermittent convexes.
Figure 12:
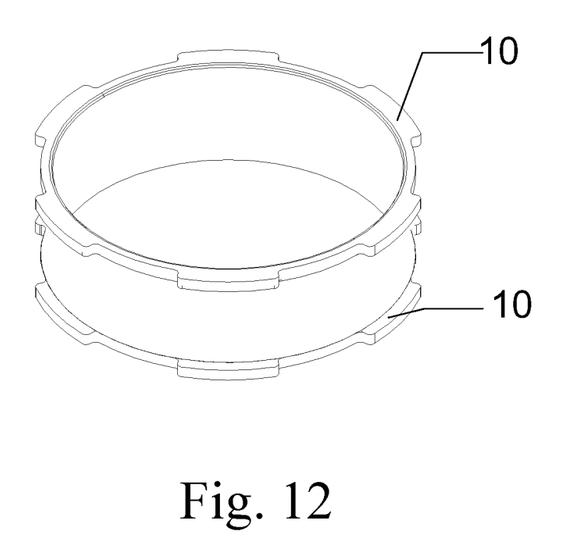
FIG. 12 is a sketch view of an inner ring, wherein both the upper and lower edges have the intermittent convexes 10.

Referring to FIG. 11, upper edges of external sidewalls of the inner ring 2 have loop convexes 9, and lower edges of the external sidewalls of the inner ring 2 have intermittent convexes 10. Referring to FIG. 12, both the upper and lower edges have the intermittent convexes 10. Alternatively, both the upper and lower edges may have the loop convexes 9.

Figure 13:
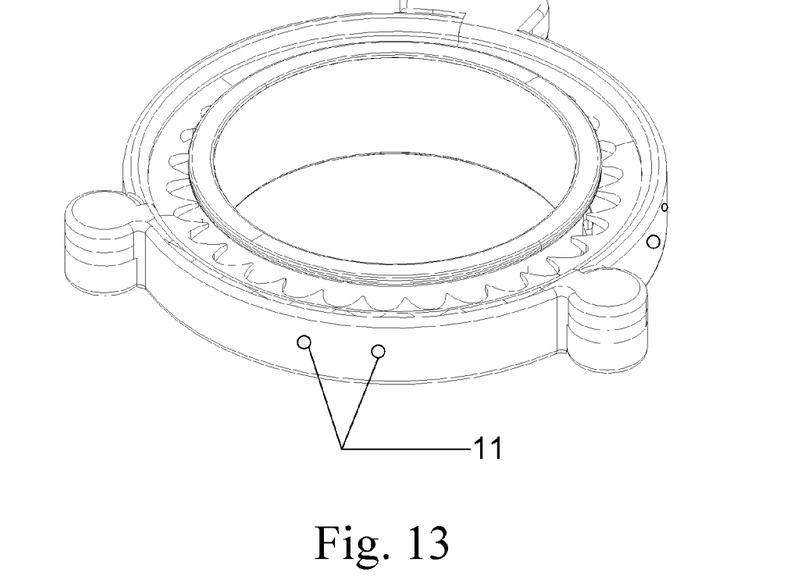
FIG. 13 is a sketch view of through-holes.

Referring to FIG. 13, the outer ring 1 has at least two through-holes 11, and the through-holes 11 are placed between the arc blades 7 and the convex structures 8. The through-holes 11 may be arranged on a same arc structure or on different arc structures. The through-holes 11 are suitable for injection.

The disposable circumcision anastomat with the through-holes 11 further comprises a fixing fiber, wherein the fixing fiber passes through one of the through-holes 11 and bypasses the inner ring 2, then passes through the other of the through-holes 11. During operation, the inner ring 2 is placed between a prepuce inner plate and a glans and adjusted. The outer ring 1 is placed at a position corresponding to the inner ring 2 and outer than a prepuce outer plate. The prepuce is adjusted to a proper position before fixing the inner and outer prepuce plates on the inner ring 2 with the fixing fiber and closing the outer ring 1. After reaching a desired result, the fixing fiber is removed, and the redundant prepuce is cut with a blade along the loop blade. With the fixing fiber, the inner and outer prepuce plates are fixed on the inner ring 2 in a better condition for adjusting a prepuce cutting range. Meanwhile, the prepuce is fixed more smoothly between the inner ring 2 and the outer ring 1 for avoiding folding.

It is known to persons skilled in the art that the closure structure 4 may be a corresponding screw hole structure, wherein a screw bolt passes through the screw hole for closing. The closure structure 4 may also be a corresponding Z-shaped structure as shown in FIG. 1, which uses a clutching effect of the Z-shaped structure for fixing. Besides, the closure structure 4 may adopt an opening plug structure, a fiber tying structure or other structures for fixing.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A disposable circumcision anastomat, comprising: an inner ring (2) and an outer ring (1) cooperating with the inner ring (2); wherein the outer ring (1) has an outer ring opening; a closure structure (4) is provided at the outer ring opening, which forms a smooth closure; wherein the outer ring (1) comprises a plurality of arc structures hinged to each other; the arc structures comprises arc sidewalls, and the arc sidewalls are connected to arc blades (7); a loop blade is formed by a plurality of the arc blades (7) with cutting edges facing inwards; convex structures (8), which extend towards a center of a loop formed by the loop blade, are repeatedly arranged on the arc sidewalls, and a width of each of the convex structures (8) is no wider than a width of any of the arc blades (7); the arc blades (7) form containing spaces (6) with the convex structures (8);
wherein the arc blades (7) form smooth arc containing spaces (6) with the convex structures (8);
wherein the convex structures (8) on the arc sidewalls are repeatedly arranged with an interval of 1.0-10.0 mm.

2. The disposable circumcision anastomat, as recited in claim 1, wherein parallel distances between the arc blades (7) and the convex structures (8) are 1.6-6.0 mm.

3. The disposable circumcision anastomat, as recited in claim 1, wherein both upper edges and lower edges of external sidewalls of the inner ring (2) have loop convexes (9) and intermittent convexes (10).

4. The disposable circumcision anastomat, as recited in claim 1, wherein the outer ring (1) is formed by two arc structures hinged to each other, wherein the arc structures are first arc structures (3); first ends of the first arc structures (3) have arc transition structures (12), and second ends of the first arc structures (3) have the closure structure (4).

5. The disposable circumcision anastomat, as recited in claim 1, wherein the outer ring (1) is formed by no less than three arc structures hinged to each other, wherein the arc structures comprises a second arc structures (5) and two first arc structure (3); first ends of the first arc structures (3) have arc transition structures (12), and second ends of the first arc structures (3) have the closure structure (4); both a first end and a second end of the second arc structure (5) have the arc transition structures (12), wherein the arc transition structures (12) at the first end of the second arc structure (5) are placed at top faces of the arc blades (7), and the arc transition structures (12) at the second end of the second arc structure (5) are placed at lower faces of the arc blades (7).

6. The disposable circumcision anastomat, as recited in claim 1, further comprising a fixing fiber, wherein the outer ring (1) has at least two through-holes (11), and the through-holes (11) are placed between the arc blades (7) and the convex structures (8); the fixing fiber passes through one of the through-holes (11) and bypasses the inner ring (2), then passes through the other of the through-holes (11).

7. A disposable circumcision anastomat, comprising: an inner ring (2), an outer ring (1) cooperating with the inner ring (2), and an elastic gasket between the inner ring (2) and the outer ring (1); wherein the outer ring (1) has an outer ring opening; a closure structure (4) is provided at the outer ring opening, which forms a smooth closure; wherein the outer ring (1) comprises a plurality of arc structures hinged to each other; the arc structures comprises arc sidewalls, and the arc sidewalls are connected to arc blades (7); a loop blade is formed by a plurality of the arc blades (7) with cutting edges facing inwards; convex structures (8), which extend towards a center of a loop formed by the loop blade, are repeatedly arranged on the arc sidewalls; a width of each of the convex structures (8) is no wider than a combination of a width of any of the arc blades (7) and a thickness of the elastic gasket, and is no narrower than a difference of the width of any of the arc blades (7) and the thickness of the elastic gasket the arc blades (7) form containing spaces (6) with the convex structures (8);
wherein the arc blades (7) form smooth arc containing spaces (6) with the convex structures (8);
wherein the convex structures (8) on the arc sidewalls are repeatedly arranged with an interval of 1.0-10.0 mm.

8. The disposable circumcision anastomat, as recited in claim 7, wherein parallel distances between the arc blades (7) and the convex structures (8) are 1.6-6.0 mm.

9. The disposable circumcision anastomat, as recited in claim 7, wherein both upper edges and lower edges of external sidewalls of the inner ring (2) have loop convexes (9) and intermittent convexes (10).

10. The disposable circumcision anastomat, as recited in claim 7, wherein the outer ring (1) is formed by two arc structures hinged to each other, wherein the arc structures are first arc structures (3); first ends of the first arc structures (3) have arc transition structures (12), and second ends of the first arc structures (3) have the closure structure (4).

11. The disposable circumcision anastomat, as recited in claim 7, wherein the outer ring (1) is formed by no less than three arc structures hinged to each other, wherein the arc structures comprises a second arc structures (5) and two first arc structure (3); first ends of the first arc structures (3) have arc transition structures (12), and second ends of the first arc structures (3) have the closure structure (4); both a first end and a second end of the second arc structure (5) have the arc transition structures (12), wherein the arc transition structures (12) at the first end of the second arc structure (5) are placed at top faces of the arc blades (7), and the arc transition structures (12) at the second end of the second arc structure (5) are placed at lower faces of the arc blades (7).

12. The disposable circumcision anastomat, as recited in claim 7, further comprising a fixing fiber, wherein the outer ring (1) has at least two through-holes (11), and the through-holes (11) are placed between the arc blades (7) and the convex structures (8); the fixing fiber passes through one of the through-holes (11) and bypasses the inner ring (2), then passes through the other of the through-holes (11).

* * * * *